(12) United States Patent
Brunner

(10) Patent No.: US 8,002,672 B2
(45) Date of Patent: Aug. 23, 2011

(54) GAIT ANALYSIS APPARATUS AND METHOD USING A TREADMILL

(75) Inventor: Wolfgang Brunner, Maierhoefen (DE)

(73) Assignee: Zebris Medical GmbH, Isny Im Allgau (DE)

( * ) Notice: Subject to any disclaimer, the term of this patent is extended or adjusted under 35 U.S.C. 154(b) by 89 days.

(21) Appl. No.: 12/251,634

(22) Filed: Oct. 15, 2008

(65) Prior Publication Data
US 2010/0035727 A1 Feb. 11, 2010

(30) Foreign Application Priority Data
Oct. 15, 2007 (DE) .......... 10 2007 049 323

(51) Int. Cl.
*A63B 71/00* (2006.01)
(52) U.S. Cl. .............................. 482/8; 482/54
(58) Field of Classification Search .......... 482/1, 8, 482/54
See application file for complete search history.

(56) References Cited

U.S. PATENT DOCUMENTS

| | | | |
|---|---|---|---|
| 4,733,068 A * | 3/1988 | Thiele et al. | 250/227.14 |
| 6,645,126 B1 * | 11/2003 | Martin et al. | 482/54 |
| 7,455,620 B2 * | 11/2008 | Frykman et al. | 482/1 |
| 2006/0009333 A1 * | 1/2006 | Wang | 482/54 |
| 2009/0062695 A1 * | 3/2009 | Sauvignet et al. | 600/592 |

FOREIGN PATENT DOCUMENTS

DE 4027317 C1 * 12/1991
* cited by examiner

*Primary Examiner* — Loan Thanh
*Assistant Examiner* — Shila Abyaneh
(74) *Attorney, Agent, or Firm* — Donald R. Boys; Central Coast Patent Agency, Inc.

(57) ABSTRACT

Gait analysis apparatus using a treadmill, comprising an endless belt, which is guided over at least two rollers and the upper surface of which serves as walking surface, a sensor system for determining a pressure/force distribution on a measurement plate located underneath the endless belt and having a plurality of pressure/force sensors arranged in a matrix on the side facing the treadmill belt, wherein the measurement plate comprising the plurality of pressure/force sensors arranged in a matrix is itself supported by at least one base force sensor and the analyzing unit comprises an additional signal input connected to a signal output of the base force sensor as well as an additional signal processing stage for processing the output signal of the or each base force sensor in terms of a calibration or correction signal processing of the output signals of the pressure/force sensors arranged in a matrix, respectively.

5 Claims, 11 Drawing Sheets

GAIT ANALYSIS APPARATUS AND METHOD USING A TREADMILL

CROSS-REFERENCE TO RELATED DOCUMENTS

Figure 1:
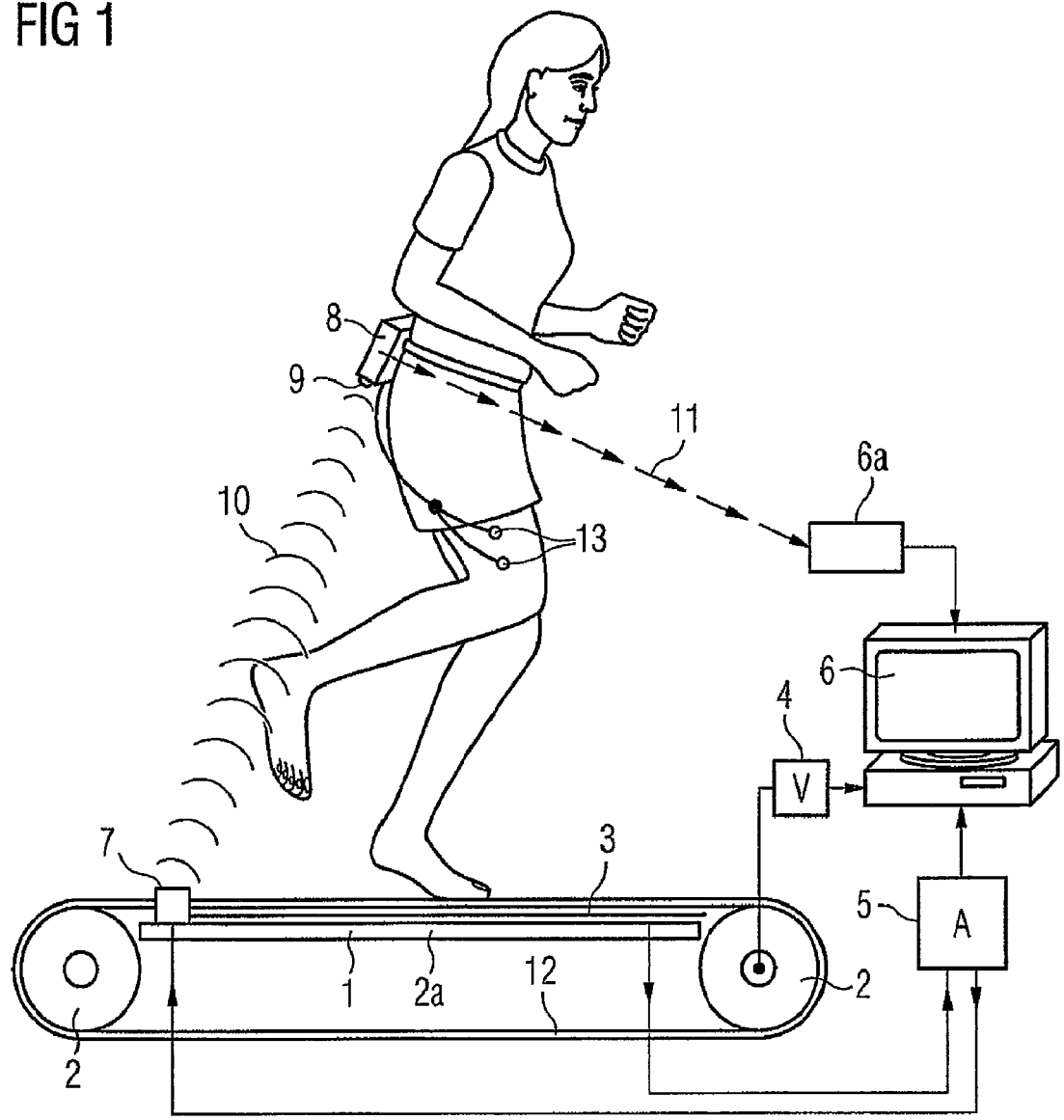

The present application claims priority to a German patent application serial number DE 10 2007 049 323.3, filed on Oct. 15, 2007, which is incorporated herein in its entirety, at least by reference.

DESCRIPTION

The present invention relates to an apparatus and a method for analyzing a gait on a treadmill.

Apparatus for the detection of pressure and force distributions are known per se, for example, from DE 36 42 088 C2 and DE 25 29 475 C3.

Many of the prior apparatus can be employed as platforms for the biomechanical gait analysis, which examine and analyze the gait of a vertebrate, especially of a human being, but also of a horse or dog etc., if necessary. There is the drawback, however, that only one single step and one single flexing action of the foot can be recorded. To obtain a natural gait behavior it is necessary, however, to record the gait over a longer time period.

Therefore, apparatus and methods for the gait analysis using a treadmill have already been proposed. Reference is here made, for example, to DE 40 27 317 C1 or U.S. Pat. No. 6,010,465 A.

Moreover, a measuring device is described as being known in R. Kram and A. J. Powell: "A treadmill-mounted force platform" Appl. Physiol. 67 (4): 1692-1698 (1989), wherein a treadmill belt is drawn over a measuring platform or measuring surface, respectively, thereby permitting a continuous detection of forces.

The first one of these publications describes a treadmill formed of a plurality of members, each of which comprises pressure or force sensors, respectively, which are arranged in a matrix, while the second publication describes a treadmill comprising a measuring plate disposed underneath the belt surface with pressure or force sensors, respectively, arranged in a matrix. Both publications teach that an analyzing unit is connected to the respective sensor system, and U.S. Pat. No. 6,010,465 describes relatively detailed the construction and the operating mode of the analyzing unit, for example, for analyzing the position and an associated force quantity when stepping onto the treadmill belt, e.g. for determining torsional moments and loads exerted on the ankle joints, as well as specific gait parameters.

It has shown that, for various reasons, the exactness of existing apparatus and methods for deriving differentiated medical and sports-physiological statements is not enough. The unpublished application PCT/EP2006010471 of the applicant therefore proposes an apparatus for the "automatic" gait analysis, which allows a highly precise detection and analysis of the gait parameters which are generated as a vertebrate (specifically a human being) is walking in a natural way.

This apparatus has proved successful, but has also revealed some problems. The apparatus comprises a plurality of relatively small sensors in the measurement plate, which, due to their small size and in view of the overall cost, can only provide for a limited measuring accuracy and long-term stability. As the treadmill belt pulls, in a way, the feet of a subject over the individual sensors of the measurement plate as he is walking or running, and as these sensors are not ideally point-shaped, but have, of course, a specific size, certain vibrations ("jittering") can be observed during the measurements as a result of the change from one sensor to the other, which superimpose the actual measured signal. Finally, as a result of the unavoidable tolerances between the individual sensors of the measurement plate, the signal measured during the time-dependent representation of the force or pressure profile of a flexing action may be subject to additional irregularities, which are noticed, for example, as "disruptions" in the force and pressure profile curves.

The apparatus according to claim 1 provides for a further improved embodiment of that apparatus, and the method according to claim 22 provides for an improved method. Useful further developments of the inventive concept are each defined in the dependent claims.

According to the invention, substantial improvements are obtained by not only equipping the measurement plate with pressure or force sensors, respectively, but also in that the measurement plate itself is supported by—comparatively few and preferably high-quality—base force sensors. Without restricting the concrete technical realization possibility these sensors will hereinafter also be referred to as load cells, these load cells also including capacitive and resistive sensors as well as strain gauges or sensors operating according to other principles. According to the invention, the signals thereof are subjected to a combined processing with those of the pressure or force sensors arranged in a matrix in the force measurement plate, so as to obtain a resultant measured signal which is more exact, more stable over a long term and/or which can be better analyzed under certain conditions.

The gait analysis apparatus proposed herein permits absolute-value measurements with a high demand on precision and comparability with measurements performed at other times, so that this apparatus allows to a substantially greater extent biomechanical long-term measurements as well as comparative measurements between different subjects or under different load conditions, respectively.

In a useful embodiment of this apparatus it is provided that the measurement plate is supported by at least three, preferably four to eight load cells. Alternatively, it is also possible to use only one supporting force or pressure sensor (one load cell) or two sensors, provided that the force measurement plate is then guided at low friction in additional guides, which are not equipped with sensors, or that the force sensors are very large with respect to their surface.

In view of the fact that high-quality load cells must typically only be loaded in one defined direction (by excluding tilting moments), the guides of the force measurement plate are to be designed with respect to the base force sensors in such a way that substantially only vertical forces act on the latter and the occurrence of tilting moments or shearing forces is avoided. The more base force sensors are employed, the less stable and lighter can the actual measurement plate, as a rule, be embodied. From this follows, of course, that the overall costs for the high-quality base force sensors do then increase and also that the analysis processing becomes more complicated. In another simple embodiment of the apparatus, the analyzing unit thereof is embodied in such a way that the processing stage for the additional signal is designed to perform the sum signal processing of the load cells. The aforementioned sum signal is the actual absolute-value signal of the force or pressure action, respectively, exerted by the subject onto the measurement plate altogether, and is basically sufficient for calibration purposes.

A further developed version of the apparatus provides that the additional signal processing stage is designed for a processing of the output signal of the or each load cell with respect to its time-dependence, to correct the time-dependent behavior of the output signals of the plurality of pressure/force sensors arranged in a matrix on the basis of a predetermined behavior correction algorithm. With this embodiment of the analyzing unit it is possible to accomplish relatively easily and advantageously a "smoothing" of the time-dependent pressure distribution images obtained with the measurement plate. Such a "smoothing" in terms of getting rid of signal artifacts, which are merely evaluated as unwanted signals, is in many respects sensible for biomechanical analyses.

As the measurement plate has an own weight and, for a combined analysis, the signals of the pressure and force sensors arranged in it in the matrix and those of the base force sensors supporting the measurement plate have to be brought to a common reference basis, the additional signal processing stage expediently comprises zero-value adaptation means, which may reasonably be combined with calibration means required anyhow in the analysis stage for the signals of the measurement plate sensors in a functional and, if necessary, also constructional manner. An adjustability is advantageous especially in view of tests with an inclined treadmill (subject walking uphill or downhill) because the weight of the measurement plate and the treadmill then has different effects in response to the angle of inclination and should be corrected in a differentiated manner.

The apparatus described herein allows to record the gait over a longer period of time because a treadmill system is used. This treadmill system comprises an endless belt drawn over a sensor platform, which is provided with a plurality of pressure and force sensors arranged in a matrix. Basically, the walking or running across such a plate does not deliver any measuring results usable for an analysis, because the pressure values vary constantly as the feet are, so to speak, drawn over the plate with the belt. However, this problem is overcome by combining the advance motion of the belt or the belt speed, respectively, with the continuously detected pressure values and by reconstructing, by means of an analyzing unit, the position of pressure distribution images, from which the gait parameters can then be determined.

In order to obtain an adequate informative result for all relevant applications, considerable precision requirements taking into account the relevant values have to be fulfilled. First, this includes the instantaneous speed of the treadmill belt, but also the signal precision of the pressure or force sensors, respectively, which is subject to a temperature dependence. According to the invention it is, therefore, initially provided to determine the instantaneous speed of the treadmill by using the pressure distribution images recorded by the sensors, i.e. by analyzing their time and position dependence. In a relatively independent development of the inventive concept, moreover, correction means are provided for the correction of the output signals of the pressure and force sensors (or, in a modification, also of the entirety of the pressure distribution images, respectively) in the event of false results caused by a rise in temperature. In this case, too, the correction is accomplished in a particularly advantageous manner by using the analysis result itself, that is, the recorded pressure distributions in dependence on the time.

In the aforementioned development of the inventive concept, in a particularly precisely working embodiment, a sensor is provided for the direct detection of the speed of the treadmill, which is connected to a second input of the speed indicator stage, and the speed indicator stage is designed to analyze the sensor signal in connection with the time and position dependence of the pressure distribution images. This design requires a slightly more complex processing, because several input signals have to be taken into account. However, apart from the potentially higher accuracy, it also offers the advantage of a plausibility check and, thus, greater reliability.

In a first embodiment of this design it is provided that the or a sensor is a speed indicator sensor on a roller of the treadmill belt. An alternative or extension to this provides for an embodiment, in which a coding pattern is provided on one side along the treadmill belt, and the or a sensor is an optical detector detecting the motion of the coding pattern. Specifically, it may be provided that the coding pattern is provided on the inner side of the treadmill belt facing the rollers, and the optical detector is mounted on the measurement plate comprising the pressure/force sensors. Under the constructional aspect, this embodiment is easy to realize and robust during operation. The coding need not necessarily be an optical one. Also a magnetic or conductivity pattern or the like may be provided on the treadmill belt, and a corresponding magnetic, capacitive, inductive or other detector may be provided.

Under this aspect of the invention it may, moreover, be provided that the or a sensor is an optical detector detecting a structure of a surface of the treadmill belt, and that the detector is assigned a pre-analyzing unit for deriving a speed measuring signal from the time and position dependence of the structure during the operation of the treadmill. This permits the use of a conventional treadmill belt material, provided that it has a structure adequately formed for an optical detection. As a separate optical coding may be waived, considerable costs can be saved as compared to the embodiment mentioned before—however, at the expense of a basically somewhat higher susceptibility to interferences.

In an advantageous embodiment of this further development of the inventive concept it is provided that the correction means comprise a correction stage, which is connected to the analyzing unit on the input side and between the pressure/force sensors and the input of the analyzing unit on the output side, for the sensor-selective calculation of pressure/force correction signals in response to the time and position dependence of the pressure distribution images.

In another embodiment it is provided that the correction means comprise a timing element for performing a dynamic correction of the measured signals of at least some of the pressure/force sensors in dependence on the operating time of the apparatus. A combination of both embodiments is characterized in that the correction stage comprises a timing element, in which a stored correction signal time curve is applied to the output signals of selected pressure/force sensors.

In another embodiment of the invention it is provided that a decoupling foil is provided between the measurement plate and the treadmill belt for mechanically decoupling horizontal pressure components or horizontal forces, respectively, to transfer substantially only vertical pressure components or vertical forces, respectively, from the treadmill belt to the sensor matrix.

This advantageously permits the use of pressure and force sensors which do not have a specific uniaxiality and would, therefore, allow—without the provision of the aforementioned decoupling foil—a certain falsification of the interesting vertical components by horizontal components. Specifically, it permits the omission of an additional sensor system for the horizontal components, which could correct such falsifications, but which would, of course, involve an increased construction and analysis expenditure.

In another embodiment, a synchronization unit is provided for synchronizing the pressure/force distribution measurement with a detection of other biometrical measured quantities carried out by separate measuring and processing means. The sensor part comprises, for example, an additional light emitter, which emits a light signal at specific points of time, preferably at each first ground contact of the feet or at defined time intervals. In a preferred embodiment the subject carries on him, e.g. on the belt, a measuring adapter for detecting other biometrical signals. This adapter includes a light receiver, which receives the light signal of the sensor plate.

Preferably, the received light signal is coded and is then superimposed, for example, on the biometrical measured signals. The measuring adapter then transmits the biometrical measured signals with the superimposed light signal wirelessly to the computer unit, in which the pressure signals of the sensor plate are represented with the biometrical signals in a time-synchronized manner. Alternatively, it is possible that the light signals are emitted by the measuring adapter and are received by the sensor plate. Also a video recording and, if appropriate, also a video analysis can be controlled in this or a similar way.

Figure 2:
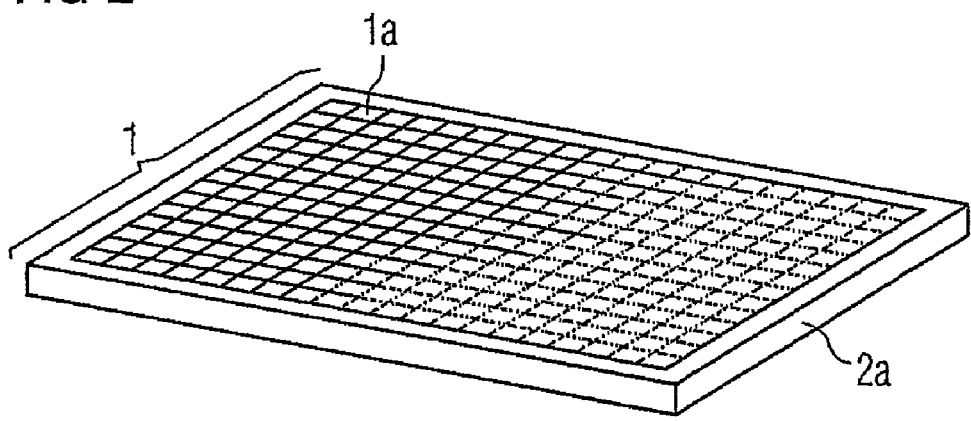
Figure 3:
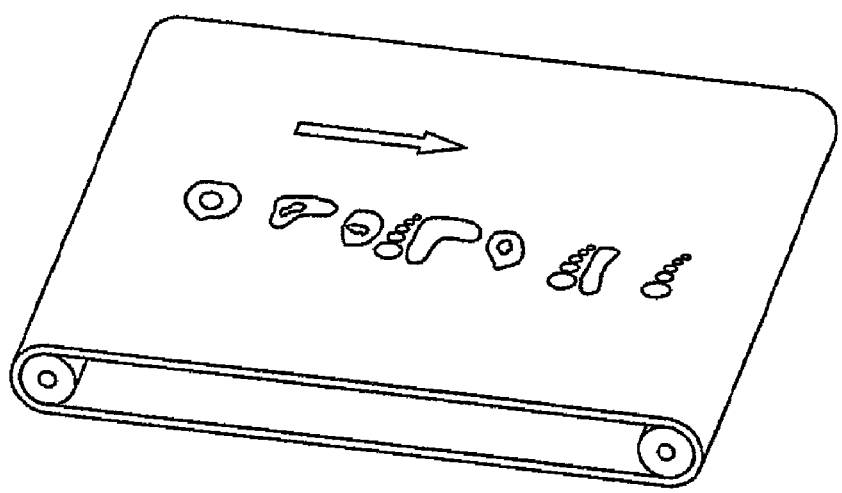
Figure 4:
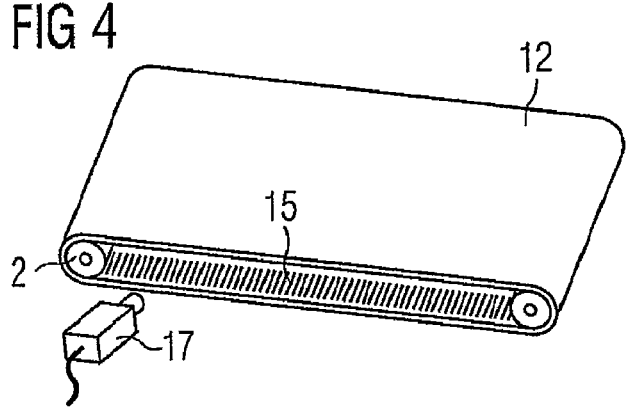
Figure 5:
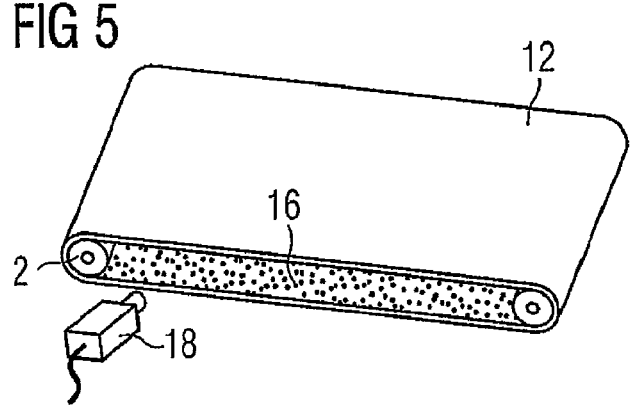
Figure 6:
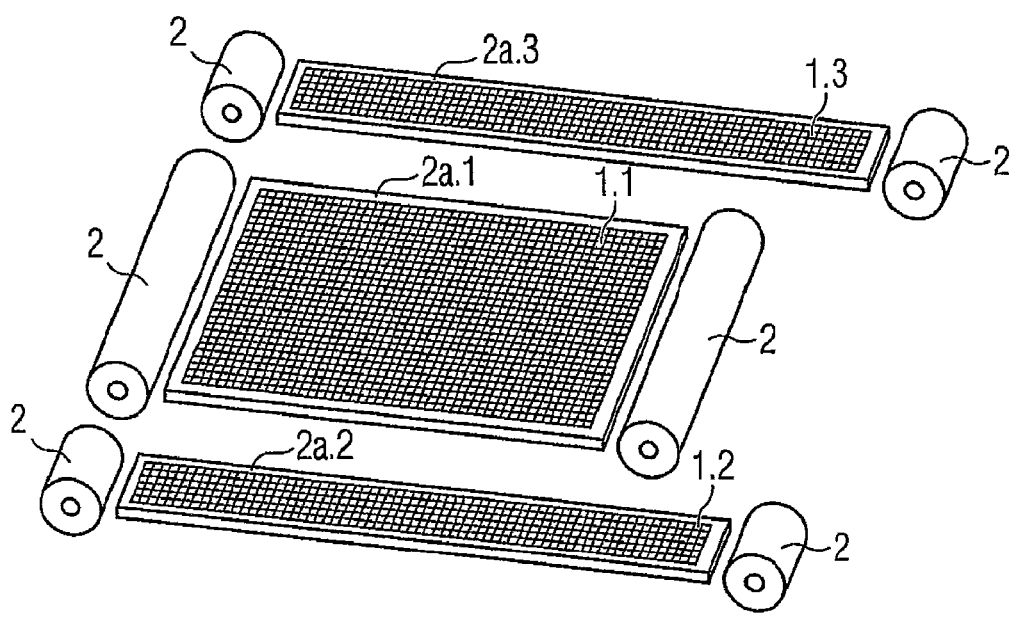
Figure 7A:
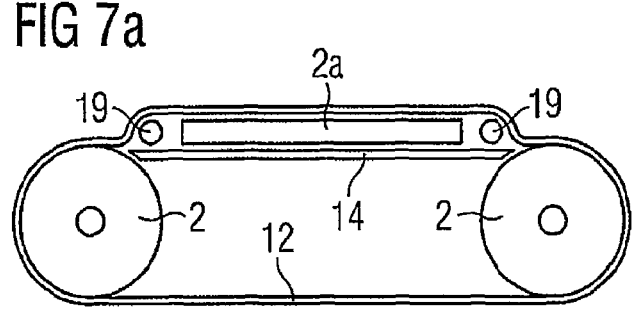
Figure 7B:
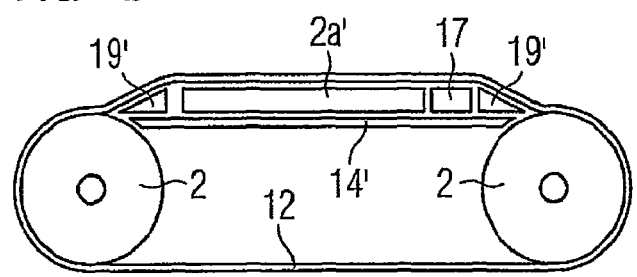
Figure 8:
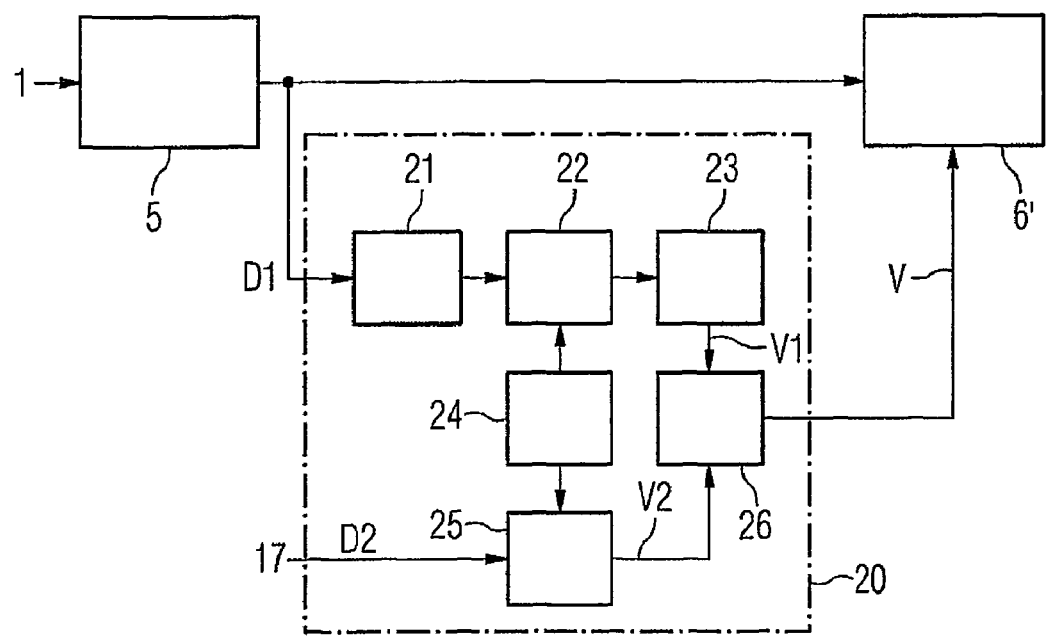
Figure 9:
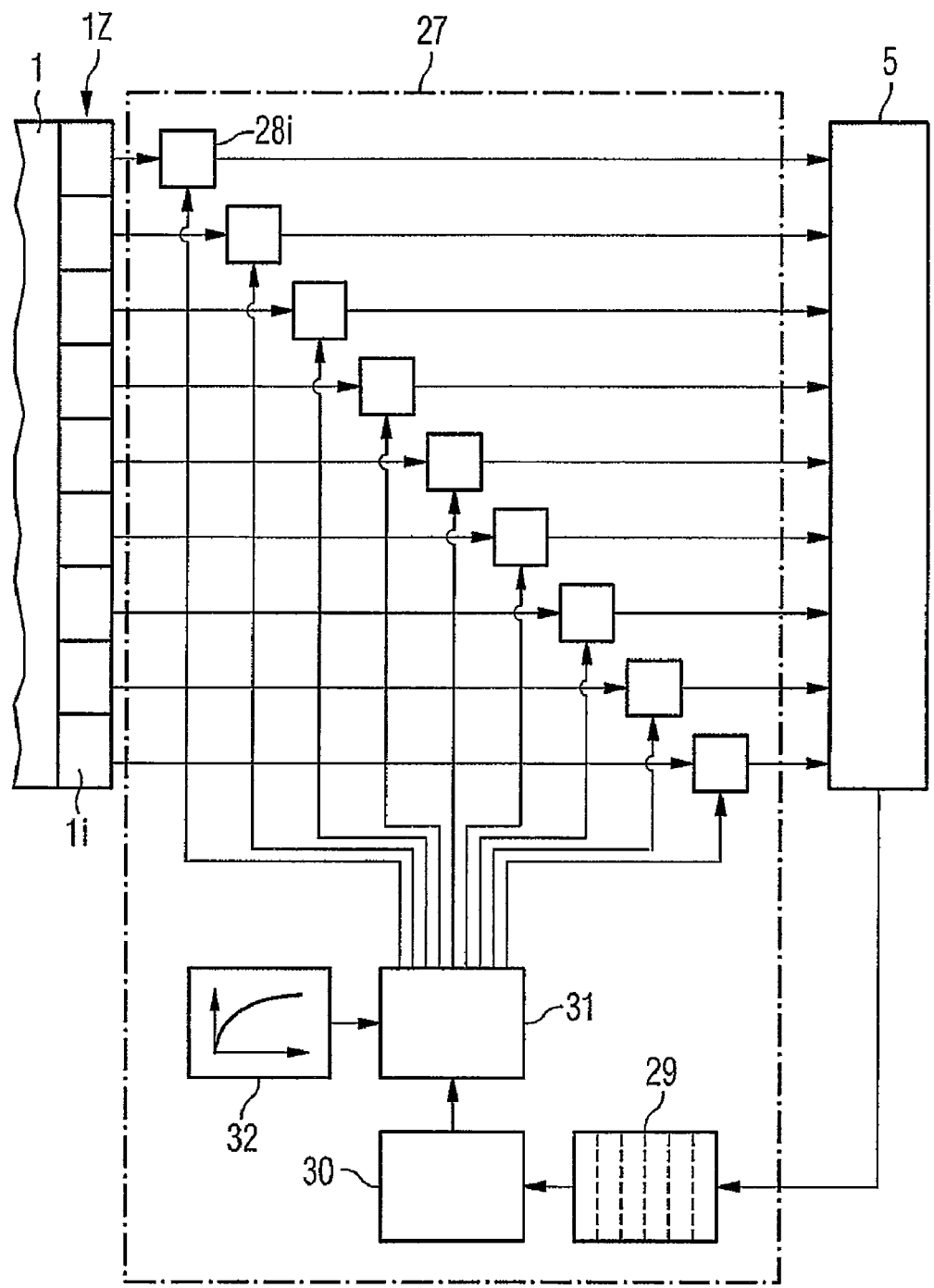
Figure 10:
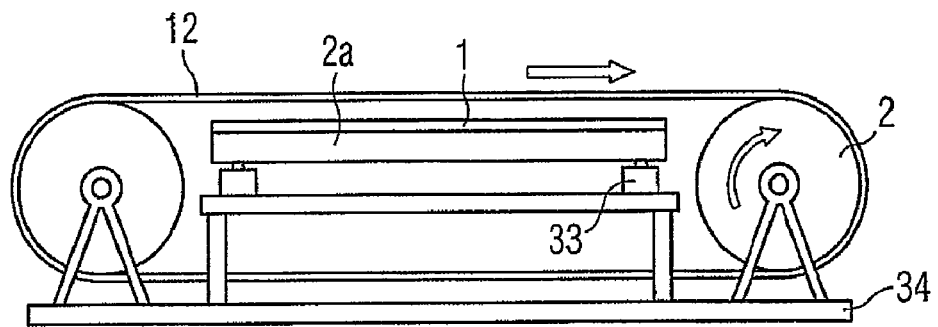
Figure 11:
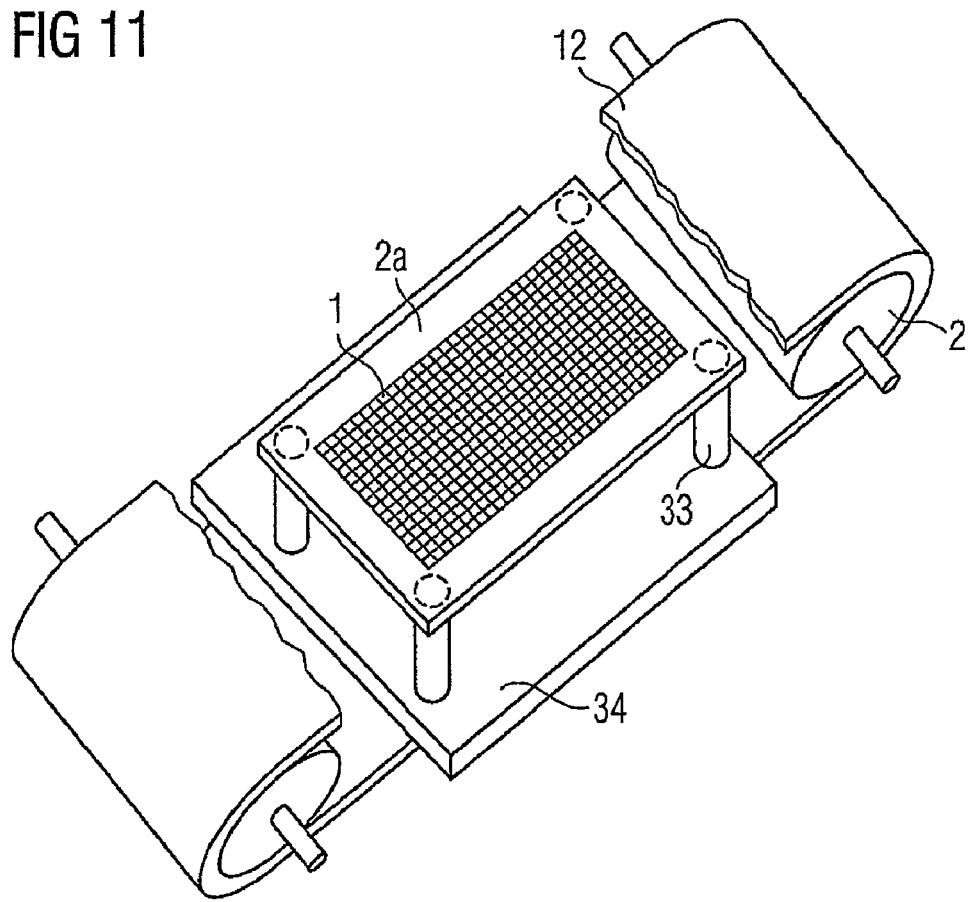
Figure 12:
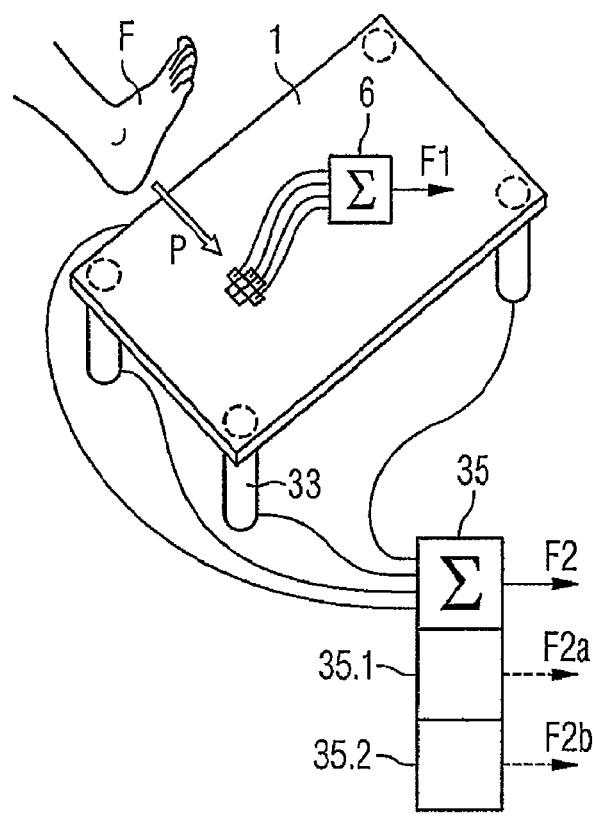
Figure 13:
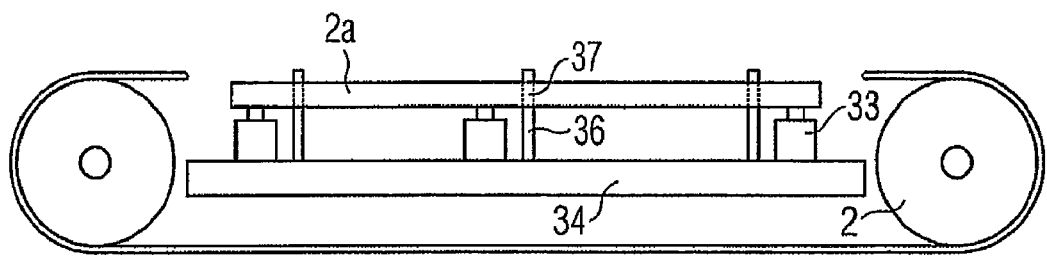
Figure 14:
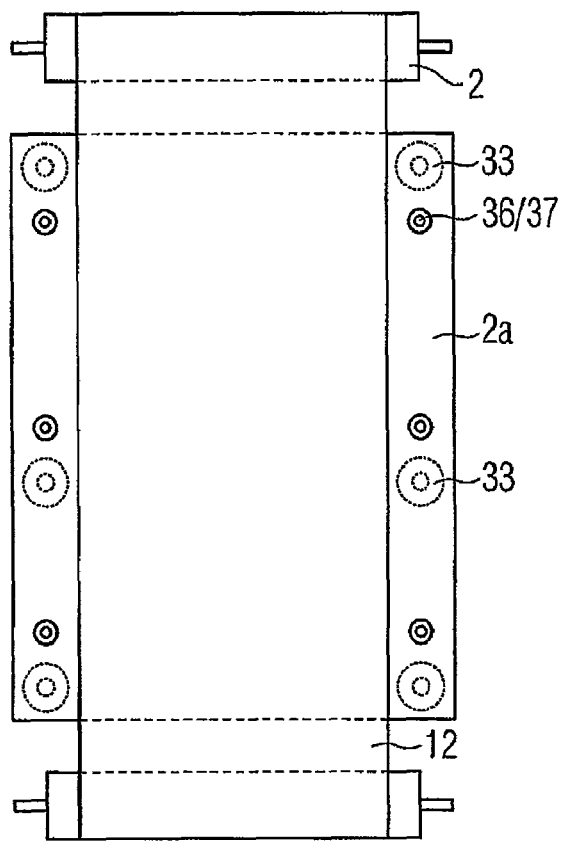
Figure 15:
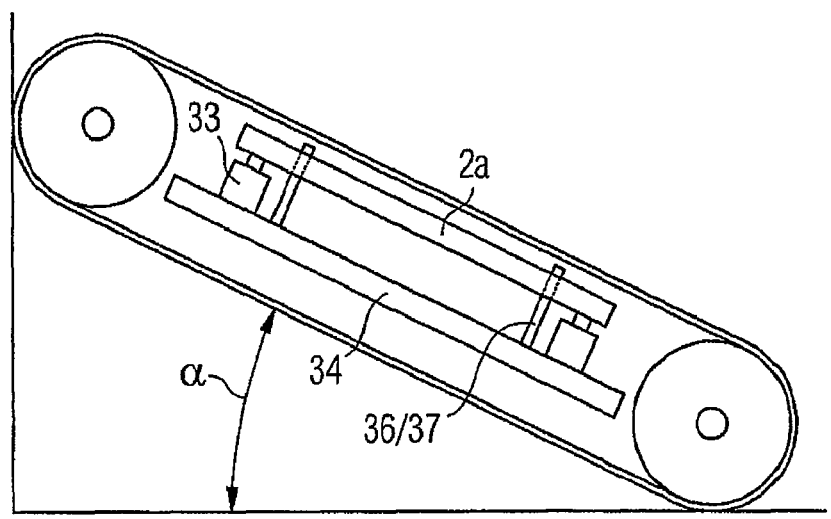
Figure 16:
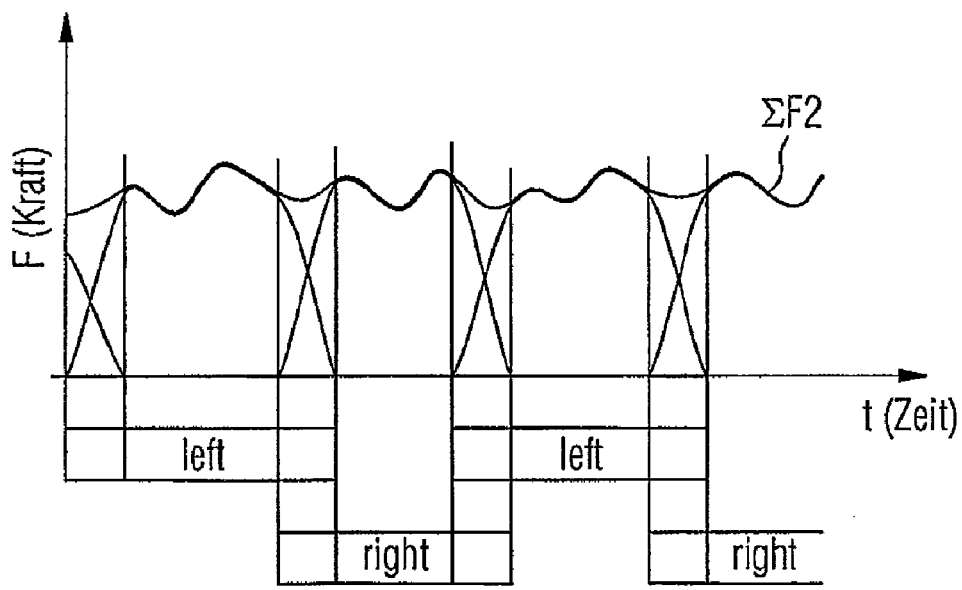
Figure 17:
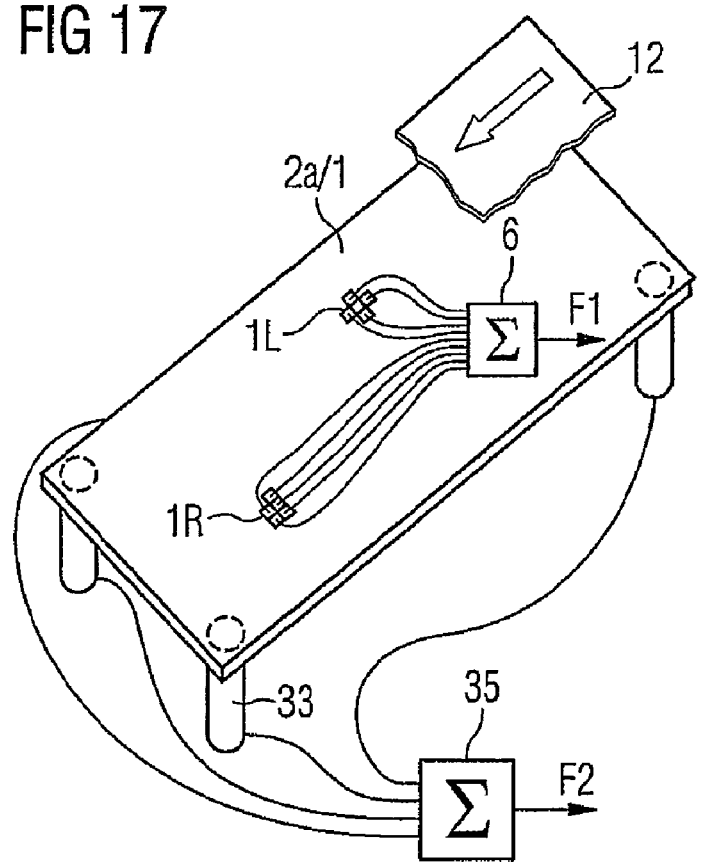
Figure 18:
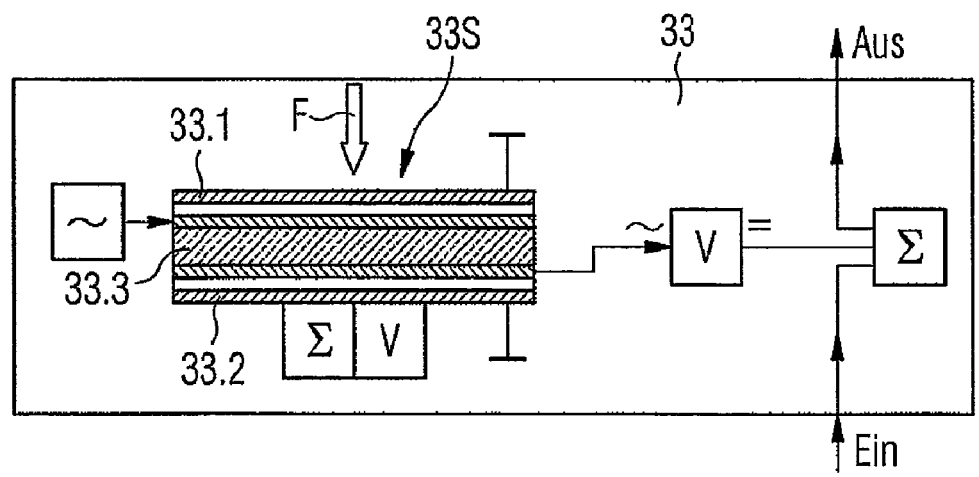
Figure 19A:
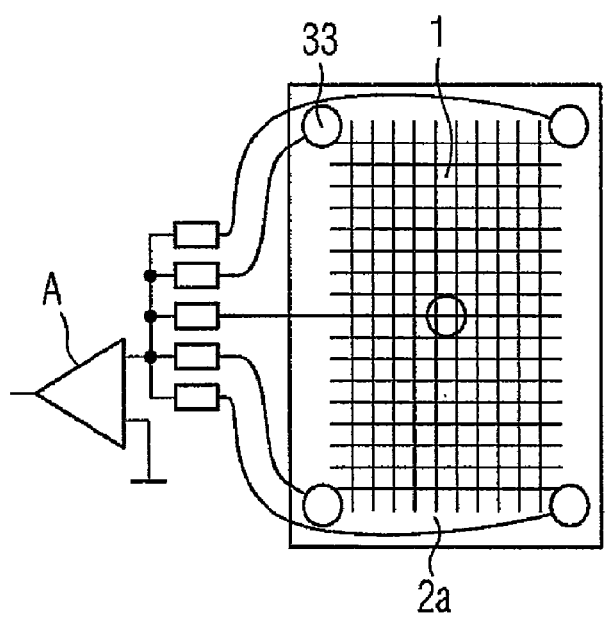
Figure 19B:
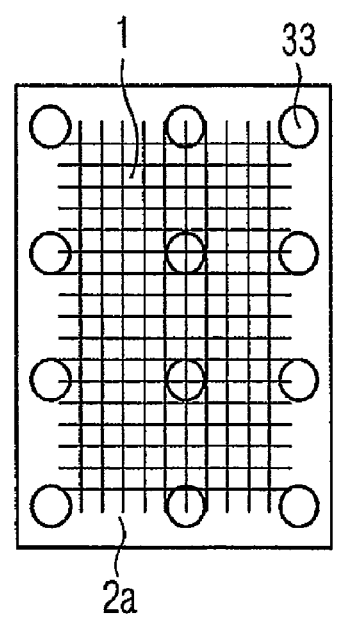
Figure 20:
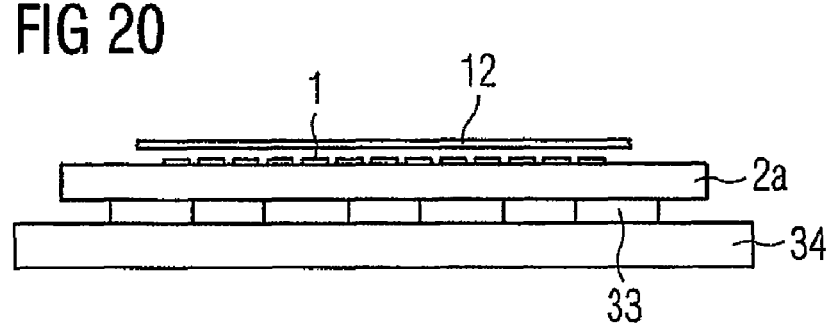
Figure 21:
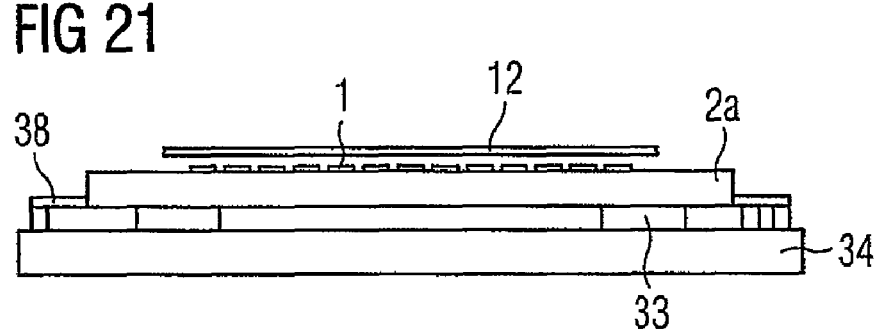
Figure 21A:
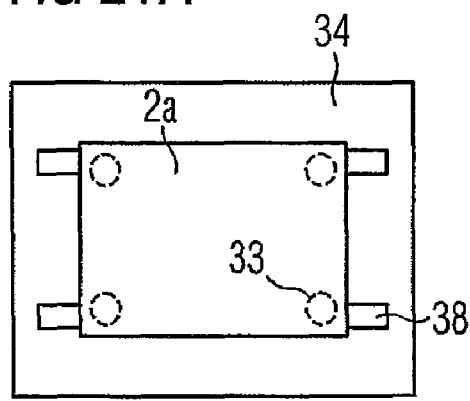
Figure 21B:
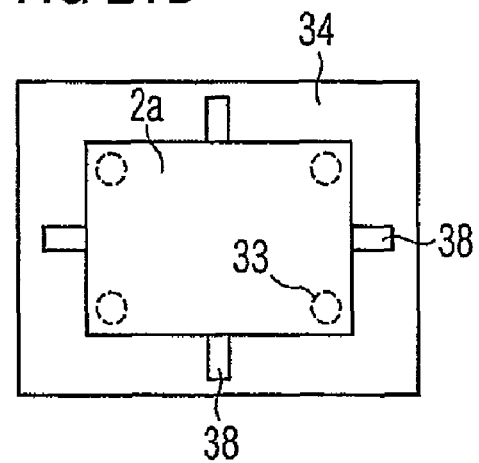

Embodiments of the inventive method and the inventive apparatus are largely analogous to each other, so that a separate description under apparatus aspects on the one hand and under method aspects on the other is not needed. Advantageous and expedient embodiments of the invention are also inferable from the dependent claims and the following description of preferred embodiments by means of the figures. In the figures:

FIG. 1 shows a schematic representation of essential parts of an embodiment of the apparatus according to the invention, FIG. 2 shows a schematic representation of the support plate of FIG. 1, FIG. 3 schematically shows a top view of the treadmill belt with pressure distribution images, FIGS. 4 and 5 show schematic representations of modified treadmill belt embodiments, comprising means to determine the speed, FIG. 6 shows an apparatus comprising several treadmill arrangements, FIGS. 7a and 7b show schematic representations of a side view type of special treadmill arrangements, FIG. 8 shows a schematic representation of an embodiment of the speed indicator stage of the processing unit, FIG. 9 shows a schematic representation of an embodiment of the correction means for correcting measured signal falsifications caused by a rise in temperature, FIGS. 10 and 11 show schematic representations of an embodiment of the apparatus according to the invention, FIG. 12. shows a schematic representation of the analysis of the force signals in an embodiment of the invention, FIGS. 13 and 14 show schematic representations of another embodiment, FIG. 15 a schematic representation of the apparatus of FIGS. 13 and 14 in a specific application, FIG. 16 shows a typical variation of a force sum signal with time, FIG. 17 shows a representation explaining the obtainment of a force sum signal from the signals of the load cells, FIG. 18 shows a specific embodiment of a load cell, FIGS. 19A, 19B and 20 show representations of another embodiment of the invention, and FIG. 21 to 21B show representations of another embodiment.

FIG. 1 shows an embodiment of the system according to the invention, with the absolute-value sensor system according to the invention having been omitted in this view (see, in this respect, FIG. 10). The treadmill system comprises a circulating band or, respectively, belt 12, which is preferably drawn over two rollers 2 by means of an active drive (not shown). However, the system according to the invention may also be used in treadmill systems in which the belt is driven by the muscular energy or the gravity of the person walking on the belt.

Underneath the upper side of the belt 12 a sensor plate 2a is mounted, over which the belt is drawn. In the illustrated embodiment, a slidable and flexible thin foil 3 is provided above the sensor plate 2a, which transfers the pressure to the sensor surface 1 in a spatially resolved manner, but protects the sensor surface 1 against the horizontal forces of the circulating belt simultaneously. The sensor plate 2a may be as thin as desired and, thus, be embodied as a sensor mat. The foil may also be connected or glued to the sensor surface 1.

The sensor surface 1 is connected via an analyzing and control unit 5 to the analyzing computer 6. The analyzing and control unit 5 is preferably located in the direct proximity of the sensor plate 2a and may be integrated in the treadmill system. The advance motion or advance speed, respectively, of the circulating belt is detected and transmitted by non-illustrated means on the basis of the rotating speed of the roller 2. This may be accomplished by an automatic transmission. The analysis substantially includes the determination of the time and location of the position of the pressure distribution images moving over the treadmill belt.

In a simple embodiment, the advance speed or the rotating speed of the rollers 2 are read on a display unit of the treadmill and are manually inputted into the computer unit 6.

FIG. 2 shows an embodiment of a measuring platform 2a comprising force or pressure sensors 1a arranged in a matrix to form the sensor surface 1. The size of the pressure sensors 1 depends on the object to be measured. If human feet are measured, preferably a sensor resolution of approximately one sensor per $cm^2$ is chosen. In a preferred embodiment sensors are chosen, which are formed of individual capacitors with an elastic dielectric, which change the capacitance upon the action of forces, or sensors changing their resistance value upon the action of forces. These sensors can be combined to rows and columns and are correspondingly controlled and read out.

FIG. 3 shows how a human foot is drawn backwards by the motion of the belt, whereby the footprints illustrated are shown in phases of motion. They correspond to the sampling rate of the sensor surface. The number of the preferred measurements per unit time is dependent on the speed at which the belt is drawn backwards. Upon a motion of the foot along the belt, preferably a plurality of measuring images are recorded. The preferred sampling rate of the sensors on the sensor plate 1 is between 30 and 100 measuring images per second.

However, the detection of the advance speed of the belt by means of the movement of the roller 2 does, in many cases, not meet the requirements of a high measuring accuracy, because the belt 12 experiences a higher friction when being stepped on, and thereby changes its motional speed. A measuring difference may also be caused by an expansion of the belt or a motion of the belt against the roller.

Therefore, the time and local positions of the pressure distribution patterns on the sensor surface 1 are detected by means of pattern recognition, by the motion of the distinct pressure patterns along the sensor surface in the longitudinal direction of the belt. A foot placed on the moving belt is automatically drawn backwards by the circulating belt and generates a pressure distribution pattern on the sensors provided underneath the belt, which moves at a specific speed along the running direction of the belt. These pressure patterns or pressure faces, respectively, can be examined continuously by the computer unit with respect to their shape and expansion, and the advance motion of the pressure patterns can be detected by means of pattern recognition and image processing with respect to the time and advance speed, respectively.

The exact knowledge of the position and the timing of the pressure distribution patterns or footprints on the belt is a prerequisite to allow the determination, for example, of the essential parameters of human gait with respect to time, location and forces. If, in addition to the pattern of the pressure distribution images, the occurring pressure values are considered, the accuracy of the time and local position determination of the feet on the belt can be increased.

Moreover, the determination of the belt speed by means of pattern recognition may be combined with other measuring methods for determining the belt speed. For example, a conventional tachogenerator may be provided on one of the rollers, and a calculated averaging of the speed signal supplied by the tachogenerator and the speed value detected from the propagation speed of the pressure distribution images may be provided. Apart from such an averaging of speed signals of different origins, also a threshold discrimination may be provided so as to realize a plausibility check and eliminate or correct possible, entirely implausible measured values obtained as a result of analyzing the pressure distribution images.

As an alternative to the use of a tachogenerator, also a detection of patterns on the surface of the belt can supply another speed signal, which may be combined with pressure distribution image signals in the above-mentioned or a similar way.

FIG. 4 shows in a corresponding embodiment the determination of the time and local position of the belt 12 and, thus, of the pressure distribution patterns by means of a coding pattern 15 provided on the belt. Preferably, this pattern is provided on the inner side along the belt, e.g. in the form of a striped pattern 15. By means of an optical detection unit 17 the motion of the striped pattern and, thus, of the belt can be detected and, on the basis thereof, the advance speed can be determined.

In another embodiment as illustrated in FIG. 5, an optical sensor 8 is used to detect surface structures 16 inherent in the material of the belt. By this, conclusions can be drawn to the motion of the belt.

In a preferred embodiment, the optical sensors 17 and 18 shown in FIG. 4 and FIG. 5 may be provided directly on or at the sensor plate 2a, so that a compact unit is obtained; compare FIG. 7b.

FIG. 6 shows a specific embodiment of a treadmill belt, which is specifically designed for analyzing a gait using sticks (walking). This treadmill comprises three separate belts 2a.1, 2a.2 and 2a.3, whereof two are provided for the use of the sticks. In one modification, the outer, narrower belts 2a.2, 2a.3—optionally also the belt in the middle—are each provided with a sensor plate 1.1, 1.2 or 1.3, respectively, so as to allow the exact examination of the coordinates of the use of the sticks during walking. The detection of the pressure distribution patterns and of the belt speeds is accomplished in accordance with the description of the above examples and is performed separately for each belt.

A similar arrangement comprising several separately installed belts may also be advantageous for application purposes, in which a differentiation between left and right of the gait of a patient or subject and, if appropriate, the provision of a differentiated feedback by the belt to the body for the left and right foot is significant. To this end, the separate belts may be adjusted, for example, to have a different tightness, or they may be realized with a belt material having different elastic properties. Besides, a predetermined feedback to the feet can also be realized by providing the sensor plate(s) with a predetermined elasticity of compression.

FIGS. 7a and 7b show two embodiments for fixing the sensor plate 2a within the treadmill system. The sensor plate 2a is mounted on a base plate 14 or 14i of the treadmill system, respectively, with the belt being guided over the sensor plate 2a and 2a' by means of deflecting rollers 19 (FIG. 7a) or deflecting wedges 19' (FIG. 7b). In the embodiment according to FIG. 7b, moreover, the mounting of the aforementioned optical sensor 17 for detecting the speed belt on the basis of a coding pattern on the corresponding base plate 14' is schematically illustrated. This arrangement has the particular advantage that existing treadmill system can be retrofitted with a measuring sensor system without great efforts.

FIG. 8 shows in a block diagram type the basic structure of a speed indicator stage 20, in which a belt speed signal V is obtained as input signal for a processing unit 6' by using pressure distribution images as a first data set D1 outputted by the analyzing unit 5 as well as detector signals as second data set D2 outputted by the optical detector 17.

In the embodiment shown, the speed indicator stage 20 comprises a pressure distribution image memory 21, which is designed as a multi-range memory for storing a sequence of pressure distribution images D1, a pressure distribution image processing unit 22 downstream of this memory, and a first speed output stage 23 assigned to the latter on the output side. Furthermore, the speed indicator stage 20 comprises a real-time generator 24, which controls both the processing of the pressure distribution image processing stage 22 and that of the detector output signals D2 in a second speed output stage 25.

The principles of the comparative processing of successively recorded pressure distribution images in the processing unit 22 are not a subject matter of the present invention and will, therefore, not be described in more detail. They are based on the mathematical convolution principle, whereby the locally associated pressure distribution patterns are represented as multi-dimensional vectors and the scalar product is formed from the same as a dimension for the analysis of their correspondence.

Output signals V1 and V2 of the two output stages 23, 25 are subjected to an averaging in an averaging stage 26 on the basis of a predetermined algorithm (which need not necessarily effect an arithmetic averaging), and the calculated result is outputted as speed signal V.

FIG. 9 shows, likewise in a block diagram type, the structure of an embodiment of a correction stage 27 for the dynamic sensor-selective correction of output signals of the pressure/force sensors 1i of the sensor surface 1 of a gait analysis apparatus according to the invention. To simplify the representation, merely one row 1Z with a plurality of individual sensors 1i of the sensor surface 1 is represented, and the figure relates to the measured signal correction of those exemplarily illustrated pressure/force sensors.

Each of the sensor elements 1i is assigned a correcting element 28i in which its output signal can be altered by a correction amount, which is calculated sensor-specifically, prior to it reaching the analyzing unit 5. On the output side of the analyzing unit 5 a pressure distribution image memory 29 associated with the correction stage 27 is provided, which is assigned a pressure distribution image comparing unit 30 on the output side. The pressure distribution image memory 29 stores over a preadjusted time period recorded pressure distribution images, and the comparing unit 30 compares the same (after a position correction calculation was performed) in order to determine which of the pressure/force sensors 1i were acted on particularly frequently and intensively during this time period. According to experience, these sensors are subject to a particularly considerable temperature rise and, thus, to corresponding measuring signal falsifications.

The processing unit 30 outputs, as a result of its processing, a table of sensor-specific correction values which, in a downstream time adaptation stage 31, are additionally subjected to a multiplicative processing by a time curve stored in a timing element memory 32. By this post-processing the temperature rise increasing as the operating time increases, and thus also the growth over time of the required correction amount or factor, respectively, is considered.

In another embodiment of the system according to the invention, additional biometrical signals of the subject to be measured are recorded by means of a measuring adapter 8 (FIG. 1). These signals may be tensions resulting from muscular action, which are recorded by electrodes 13. Also, they may be joint angles or inclination angles recorded by electric goniometers. The measured data are preferably transmitted by a radio signal 11 to a receiver 6a of the computer unit 6.

With regard to the representation of the biometrical signals on the computer unit 6 it is significant that these are represented together with the pressure distribution values of the sensor plate 2a in a time-synchronized manner. In the embodiment shown, the control unit 5 transmits, to this end, via a light emitter of the sensor plate 7 a light signal, preferably as infrared light 10, to a light receiver 9 in the measuring adapter 8. The light signal 10 can, for example, be transmitted each time the foot of a subject hits the sensor surface.

The preferably coded light pulses 10 are converted into electrical data, superimposed on the biometrical measuring signal and transmitted by radio signal 11 to the computer unit. The coding of the light pulses can be accomplished, for example, by transmitting pulses at a specific short time interval. Then, the biometrical signals 13 are represented together with the pressure distribution values in the computer unit 6 in a time-synchronized manner.

A numerically coded time stamp is transmitted, which brings the data of the two systems, both measuring independently of each other (gait analysis and biometrical measurement), into a time synchronism. As both systems perform their measurements in a respectively known time pattern, a correct assignment between them over the whole measuring time is possible as soon as one single coding was correctly transmitted (even if a great number of synchronization attempts should have failed during the measuring period). The proposed synchronization is therefore characterized by an extreme reliability and robustness FIGS. 10 and 11 show in a schematic cross-sectional and a partially cutoff perspective representation the inventive mounting of the sensor plate 2a of the apparatus shown in FIG. 1 on absolute-value force sensors, herein on four load cells 33 disposed near the corner points of the plate on a bottom plate 34. As was already shown in FIG. 1, the apparatus further comprises two rollers 2, about which the belt 12 is looped, underneath the upper side of which the sensor plate 2a with the sensor surface 1 is located.

FIG. 12 illustrates in a sketch-like manner that the pressure p exerted by a foot F onto the measurement plate 2a is, on the one hand, detected in a spatially resolved manner by the pressure or force sensors 1i arranged in a matrix and is processed in the downstream computer unit 6, and that, on the other hand, the pressure is recorded by the four load cells 33, and the measured values thereof are processed in an additional signal processing stage 35, wherein the two computer units and processing stages 6 and 35, respectively, supply a first output signal F1 and a second output signal F2, respectively. The additional signal processing stage 35 may be regarded as an additional component of the computer unit 6 or, respectively, may be connected to the same. As is illustrated in FIG. 12 merely in a sketch-like manner, the additional signal processing unit 35 comprises a sum signal processing component 35.1 and a time-dependence processing component 35.2, which can supply to the computer unit 6 a first and second correction or compensation signal F2a and F2b, respectively, for the analysis of the time-dependent pressure distribution images recorded by the sensor plate 2a.

In the apparatus as proposed, the forces exerted in each load phase on the pressure sensors being right now in use (here at heel contact) are added up. At the same time, those forces are added up, which are introduced into the load cells. In a preferred embodiment, the pressure distribution sensors are additively linked by a software in a computer unit, and the output voltages of the load cells are added to a simple electrical circuit and supplied after an A/D conversion to the computer unit (not illustrated). It is assumed that the values of the load cells are more precise. Therefore, a target-actual comparison is now performed. Accordingly, the pressure values of each individually used pressure sensor of the measuring matrix are corrected by the percentage of the deviation.

As it might be known in which force ranges the pressure sensors of the measuring matrix are particularly exact or inexact, they are corrected, in a specific embodiment, by different percentages, depending on the indicated pressure value. If the total deviation between the target force and the actual force is, for example, 10%, the sensors exposed to a high pressure load can be corrected upwardly or downwardly, for example, by 12%, and the sensors exposed to a low pressure load, for example, only by 9%.

In one embodiment, the output signals of the load cells may additionally be processed separately, whereby the point of the force application of the forces acting on the measurement plate can be determined, if any.

FIGS. 13 and 14 show in a schematic cross-sectional representation and a schematic top view, respectively, another embodiment, in which the reference numbers for components explained above have been maintained and shall not be explained again herein. In order to guarantee a force input into the high-quality load cells 33 in accordance with a strictly predetermined direction of action, guide pins 36 are provided on the bases plate 34, each of them being associated with a load cell 33 and engaging corresponding bores 37 in the measurement plate 2a. This ensures a lateral guidance of the measurement plate relative to the base plate 34 in both the X- and Y-direction and, thus, a force input into the load cells 33 exactly in the Z-direction. Besides, the system illustrated in FIG. 13 to 15 differs from the aforementioned embodiment in that a total of six load cells are provided, that is, the measurement plate 2a is supported with respect to the bottom plate 34 at more points and can, therefore, be constructed less rigidly and thus lighter and more inexpensively.

FIG. 15 illustrates how the apparatus of FIGS. 13 and 14 can be inclined by an angle α in order to examine the gait of a subject as he walks uphill and downhill. It will be appreciated that, in this position, a portion of the vertical forces is not recorded by the load cells 33, but by the pin/bore guides 36/37, and that, by this, the measured result is falsified to a certain degree. For small inclination angles α the falsification is neglectable. According to the invention, the force vector can be determined and the force value corrected in dependence on the angle of inclination of the treadmill.

FIG. 16 shows a typical variation of a force sum signal F with time, as is typical for the normal human gait—with a time overlap of the steps made with the left and right foot ("left" and "right", respectively). Within the scope of the invention, the force sum signal can be obtained from the output signals of the base force sensors. As the load cells measure the total force, it is obvious to use for these force curves not the sum signals of the pressure distribution sensors (F1), but the more exact sum signals of the load cells (F2) right away.

FIG. 17 serves to explain this procedure, in which, merely for illustrative purposes, a part sensor field 1L loaded by the left foot and a part sensor field 1R loaded by the right foot are shown on the measurement plate 2a. This results in the problem that, during normal walking, both feet are on the treadmill belt simultaneously in specific time segments. Thus, the total force F2 cannot be used directly. In a special procedure, therefore, the results of the pressure distribution sensors are analyzed first, whereby the computer unit identifies the prints according to the left and right side of the body and calculates the timing. Then, at the times when both feet are placed on the belt, the corrected force values Ft, and at the times when the plate is loaded by the left or right foot alone, the force values F2 are represented. Taking into account the pressure patterns in connection with the determination of the force F2 may be an advantage for further analyses.

The identification of the prints and, thus, of the force sum signal according to the left and right side of the body can be performed in different manners. For example, the prints may be identified by the examiner and assigned to the sides of the body. It is likewise possible, however, to identify only the first print and to then assign the other ones automatically to the left and right side of the body, because these have, of course, to take place alternately. Also, it is particularly preferred to assign the first or all prints automatically to the correct side of the body by means of the computer unit. This may be achieved with a recognition of the print pattern of the feet. Moreover, it is possible to perform an analysis whether the footprints can be localized more on the left or more on the right side, and to make the assignment accordingly.

This analysis may include a weighting according to the dimensions of the prints, the pressure values or the point of gravity or force application, respectively.

Furthermore, it may be sensible to record a whole time segment with multiple flexing actions and to perform the corresponding analysis and assignment afterwards, or to combine different ones of the aforementioned methods.

As a rule, double loading phases do not occur if the walk is faster, so that the force values F2 can be represented directly. Merely the assignment to the left and right side of the body is performed with the aid of the pressure distribution values.

FIG. 18 shows as a specific embodiment a load cell 33 comprising a capacitive sensor 33S with two capacitor plates 33.1 and 33.2 and an elastic dielectric 33.3. In this embodiment, the base force sensor may be designed very flatly, and in the embodiment as illustrated a signal processing stage and an adder (in analog or digital form) are integrated as well, so that this load cell can be easily incorporated into a system of the type outlined in FIG. 12 to detect a force sum signal. However, contrary to the embodiment shown therein, with linked integrated adders. The integration of summers in or on the force sensor is, of course, also advantageous if load cells are used, which operate according to other measurement methods, e.g. with strain gauges. If no digital adding up is used, both the current and voltage signals can be added up. The particular advantage resides thereby in the simple wiring, which then only has to be looped through from load cell to load cell.

FIGS. 19A, 19B and 20 show another embodiment, in which, by using five load cells (FIG. 19A) and twelve load cells (FIG. 19B), the base force sensor system is integrated in the respective measurement plate 2a. To this end, a flat design of the load cells 33 (as is symbolically illustrated in FIG. 20) is advantageous. As is once again schematically shown in FIG. 19A, in this case, too, the signals of the individual load cells are added up to form the force sum signal (total force). Specifically in the system shown in FIG. 19B, a combination by rows or columns of the load cells is possible in the favor of control and analysis. The great number of supporting points in the last-mentioned embodiment permits a particularly thin and light construction of the measurement plate 2a (pressure distribution plate).

FIG. 21 shows in a schematic representation essential components of another embodiment of the apparatus as proposed, as a modification of the embodiment illustrated in FIG. 20. In contrast to the same, the number of the load cells 33 supporting the measurement plate 2a with the sensors 1 arranged in a matrix is reduced, and an additional lateral guidance on the bottom plate 34 is realized with leaf spring elements 38. The leaf spring elements 38 absorb possible shearing or horizontal forces, thereby keeping them away from the load cells 33. Moreover, they can generate a certain preload of the measurement plate 2a with respect to the bottom plate 34, which can then be easily corrected again when determining the actual action of the pressure or the forces, respectively, as the subject is walking or running, because the spring constants of the leaf springs (or similar spring elements) are known.

Depending on the actual selection of the leaf springs or other flexion spring elements and their chosen attachment to the measurement plate, on the one hand, and the bottom plate, on the other hand, different physical arrangements are possible, of which two forms are outlined in FIGS. 21A and 21B. While in the arrangement shown in FIG. 21A four longitudinal, leaf spring elements 38 are mounted on the corner points of the measurement plate 2a in alignment with each other, FIG. 21B shows an alternative physical arrangement, in which two of the leaf spring elements are disposed in the center of the short sides of the measurement plate 2a and are oriented in alignment with each other in the X-direction, whereas two other leaf spring elements are disposed in the center of the longer sides of the measurement plate 2a and are oriented at right angles, i.e. in alignment with each other in the Y-direction.

Similar arrangements are, moreover, possible with hinge elements, which have no resilience and do, therefore, not preload the measurement plate with respect to the bottom plate, so that they do not require any correction of this preload.

The realization of the invention is not limited to the above-described examples and emphasized aspects, but is also possible in a plurality of modifications lying within the skills of the competent skilled person. Specifically, all technically possible combinations of the features of the individual claims shall be considered as being within the scope of protection of the invention.

LIST OF REFERENCE NUMBERS

1; 1.1; 1.2; 1.3 pressure/force distribution sensor surface
1$i$ sensor
1Z sensor row
2 rollers
2a; 2a.1; 2a.2; 2a.3 sensor plate/sensor mat
3 foil for absorbing the horizontal forces
4 detector for the rotating speed of the roller
5 control unit
6, 6$i$ computer unit 6a receiver
7 light emitter
8 measuring adapter
9 light receiver
10 light pulses
11 radio signal
12 belt
13 electrode
14 base plate of treadmill
15 coding pattern
16 surface structure of the belt
17; 18 optical detector
19 deflecting roller
19' deflecting wedge
20 speed indicator stage
21 pressure distribution image memory
22 pressure distribution image processing stage
23 speed output stage
24 real-time generator
25 speed output stage
26 averaging stage
27 correction stage
28i correcting element
29 pressure distribution image memory
30 pressure distribution image comparing unit
31 time adaptation stage
32 timing element memory
33 load cell
34 bottom plate
35 additional signal processing stage
35.1 sum signal processing component
35.2 time-dependence processing component
36 guide pin
37 bore
38 leaf spring element
F foot
F1, F2; F2a, F2b force signals

The invention claimed is:

1. Gait analysis apparatus using a treadmill, comprising;
an endless belt guided over at least two rollers, having an upper surface which serves as walking surface;
a sensor system configured to determine a pressure/force distribution on a measurement plate located underneath the endless belt and having a plurality of pressure/force sensors arranged in a matrix on a side facing the treadmill belt;
an analyzing unit connected to the pressure/force sensors on an input side, generating pressure distribution images from data received from the pressure/force sensors and detecting positions of the pressure distribution images from a vertebrate walking on the treadmill belt;
a processing unit, which is connected to the analyzing unit on an input side and generates measuring parameters for characterizing the gait of the vertebrate from a time and position dependence of the pressure distribution images; and
at least one base force sensor;
wherein the measurement plate comprising the plurality of pressure/force sensors is directly supported by the at least one base force sensor and the analyzing unit comprises an additional input signal from each signal output of the at least one base force sensor and a signal processing stage for processing the output signal of each base force sensor by the processing unit, and determining a calibration or correction of the output signals of the pressure/force sensors.

2. Gait analysis apparatus according to claim 1, wherein the measurement plate is supported by at least three to eight base force sensors.

3. Gait analysis apparatus according to claim 1, including an optical detector for detecting a structure of a surface of the treadmill belt and the detector derives a speed measuring signal from a time and position dependence of the structure during the operation of the treadmill.

4. Gait analysis method using a treadmill comprising the steps of;
(a) measuring vertical pressure components or vertical forces, occurring as a vertebrate is walking across an endless treadmill belt, in a spatially resolved manner by means of a measurement plate located underneath the endless belt and having a plurality of pressure/force sensors arranged in a matrix;
(b) deriving pressure images from the measurements of step (a) with respect to their time and position dependence;
(c) generating measuring parameters for characterizing the gait from the time and position dependence of the pressure distribution images; and
(d) performing a calibration or correction of the measured vertical pressure components or vertical forces, obtained as an output signal of the pressure/force sensors according to second output signals of base force sensors supporting the measurement plate.

5. Gait analysis method according to claim 4, wherein determination of instantaneous belt speed is performed by using time-dependent measuring signals recorded directly at the treadmill belt by a sensing belt structure with an optical sensor.

* * * * *